US008564784B2

(12) United States Patent
Wang et al.

(10) Patent No.: US 8,564,784 B2
(45) Date of Patent: Oct. 22, 2013

(54) LARGE AREA OPTICAL DIAGNOSIS APPARATUS AND OPERATING METHOD THEREOF

(75) Inventors: William Wang, Taoyuan (TW); Chung-Cheng Chou, Luzhu Township, Taoyuan County (TW); Che-Liang Tsai, Taichung (TW)

(73) Assignee: Crystalvue Medical Corporation, Gueishan, Taoyuan ( * ) Notice: Subject to any disclaimer, the term of this patent is extended or adjusted under 35 U.S.C. 154(b) by 75 days.

(21) Appl. No.: 13/204,132

(22) Filed: Aug. 5, 2011

(65) Prior Publication Data

US 2012/0033211 A1    Feb. 9, 2012

(30) Foreign Application Priority Data

Aug. 6, 2010 (TW) .................................. 99126315 A

(51) Int. Cl.
 *G01B 9/02* (2006.01)
(52) U.S. Cl.
 USPC ......................................... 356/450; 356/477
(58) Field of Classification Search
 USPC ............ 356/477, 478, 450, 511, 496; 372/92, 372/98, 99
 See application file for complete search history.

(56) References Cited

U.S. PATENT DOCUMENTS

| 5,343,489 A * | 8/1994 | Wangler .......................... 372/93 |
| 5,491,552 A * | 2/1996 | Knuttel .......................... 356/495 |
| 5,661,737 A * | 8/1997 | Hecht et al. ..................... 372/23 |
| 5,784,352 A * | 7/1998 | Swanson et al. ................ 369/94 |
| 5,861,991 A * | 1/1999 | Fork ............................. 359/618 |
| 6,490,046 B1 * | 12/2002 | Drabarek et al. ............. 356/489 |
| 6,956,886 B1 * | 10/2005 | Patel .............................. 372/92 |
| 7,023,557 B2 * | 4/2006 | VanWiggeren et al. ...... 356/477 |
| 7,283,248 B2 * | 10/2007 | Hill .............................. 356/498 |
| 7,362,432 B2 * | 4/2008 | Roth ............................. 356/317 |
| 7,417,740 B2 * | 8/2008 | Alphonse et al. ............. 356/479 |
| 2009/0218514 A1 * | 9/2009 | Klunder et al. ............ 250/459.1 |

* cited by examiner

*Primary Examiner* — Gregory J Toatley
*Assistant Examiner* — Shawn Decenzo
(74) *Attorney, Agent, or Firm* — Patterson & Sheridan, LLP

(57) ABSTRACT

A large area optical diagnosis apparatus and the operating method thereof are disclosed. The large area optical diagnosis apparatus includes a light source, a light path structure, and a sensing module. The light source is used to at least emit a coherent light. The light path structure includes a plurality of optical units used for dividing the coherent light into a plurality of first incident lights and a plurality of second incident lights. The plurality of first incident lights are emitted toward an object to be diagnosed and the plurality of second incident lights are emitted toward a reference end. The object to be diagnosed and the reference end reflect the plurality of first incident lights and the plurality of second incident lights to be a plurality of reflected lights. The sensing module senses the plurality of reflected lights to generate a sensing result related to the object to be diagnosed.

10 Claims, 9 Drawing Sheets

LARGE AREA OPTICAL DIAGNOSIS APPARATUS AND OPERATING METHOD THEREOF

BACKGROUND OF THE INVENTION

1. Field of the Invention

The invention relates to optical diagnosis, in particular, to a large area optical diagnosis apparatus and operating method thereof using re-designed light path structure and signal analysis unit to achieve the effect of synchronous multi-point optical coherence tomography (OCT) diagnosis.

2. Description of the Prior Art

In recent years, with the continuous progress of optical diagnosis technology, the optical image scan technology provides a non-invasive way to understand the composition and structure of the tissue of the object to be diagnosed. Because it has features of rapid and non-invasive, it is widely used in many regions, especially in medical diagnosis region. When the light is emitted into the tissue structure, with the various media in different depths, the light absorption characteristic and scattering characteristic will be also changed accordingly. And, the optical image scan technology uses different optical methods to obtain the data carried by the scattered photons in the tissue to generate high-resolution image.

In general, the medical imaging technology is used to measure the physical characteristic change generated after the physical field source is provided to the tissue and convert it into visual images. By doing so, the abnormal state of the tissue structure can be clinically judged in a qualitative and quantitative way and dynamic functional assessment can be done to provide rapid and correct diagnosis and treatment of disease, therefore, quality of medical care can be enhanced. In the trend of the medical imaging technology, the non-ionizing energy field source is used to measure and imaging in a non-invasive way to have high space resolution and contract resolution, and real-time image displaying.

In the known medical imaging technologies, a medical imaging technology called optical coherence tomography (OCT) is used to measure the coherence property of the scattering light field strength in the depth direction of the tissue and further generate 2-D or 3-D images via the low coherence light source and the measurement structure of change optical path difference interferometer. Since the OCT medical imaging technology can meet the developing requirements of the trend of the medical imaging technology, the OCT medical imaging technology is widely researched and used in many application regions.

In practical applications, because the OCT medical imaging technology has advantages of high resolution, high sensitivity, non-ionizing energy field source, low cost, and it can measure the cross-sectional structure of the tissue in the object to be diagnosed and the flow-rate distribution diagram. Therefore, it can provide image with micro level resolution to help the diagnosis of tissue disease and the positioning of the cell structure, such as the retinal of eye-ball.

Please refer to FIG. 1. FIG. 1 illustrates a schematic figure of the basic structure of the conventional time-domain OCT diagnosis apparatus. In order to generate the light path difference between the reference end and the object to be diagnosed end, the OCT diagnosis apparatus needs not only some complicated optical components, but also a shifting mechanical structure to generate the light path difference.

In addition, as shown in FIG. 1, the conventional OCT diagnosis apparatus 1 includes a light source 10, a light coupling unit 12, a reflection mirror 14, an object to be diagnosed 16, a light sensing unit 17, and a data processing unit 18. The conventional OCT diagnosis apparatus 1 changes the position of the reflection mirror 14 (movement parallel to z-direction or rotation) to obtain different light path difference, and obtains sensing result of the object to be diagnosed 16 in the depth direction (z-direction) through Michelson interference effect.

Afterward, another frequency-domain OCT diagnosis apparatus is developed. The frequency-domain OCT diagnosis apparatus includes specially designed sensing/receiving unit to obtain the interference comparing result between the reference signal and the reflected signals from different depths of the object to be diagnosed. However, no matter the above-mentioned time-domain or frequency-domain OCT diagnosis apparatus, a galvo-mirror is needed in the light path to change diagnosis points, and the structure of the OCT diagnosis apparatus will become complicated. In addition, because the time-domain and frequency-domain OCT diagnosis apparatus can only diagnose the diagnosis points one by one, it fails to perform a large-area diagnosis at the same time, so it is time-consuming and inconvenient, and has limitations in practical applications.

Therefore, the invention provides a large area optical diagnosis apparatus and operating method thereof to solve the above-mentioned problems.

SUMMARY OF THE INVENTION

A scope of the invention is to provide a large area optical diagnosis apparatus. In fact, the large area optical diagnosis apparatus is used to diagnose an object to be diagnosed, so that the optical data of the vertical cross-section of the object to be diagnosed can be obtained.

The first embodiment of the invention is a large area optical diagnosis apparatus. In this embodiment, the large area optical diagnosis apparatus includes a light source, a light path structure, and a sensing module. The light source is used for at least emitting a coherent light. The light path structure includes a plurality of optical units used for dividing the coherent light into a plurality of first incident lights and a plurality of second incident lights. The plurality of first incident lights is emitted toward an object to be diagnosed and the plurality of second incident lights is emitted toward a reference end. The object to be diagnosed and the reference end reflecting the plurality of first incident lights and the plurality of second incident lights to be a plurality of reflected lights respectively. The sensing module is used for sensing the plurality of reflected lights to generate a sensing result related to the object to be diagnosed.

In practical applications, the sensing module includes a plurality of sensing units corresponding to the plurality of reflected lights respectively. The sensing module generates the sensing result according to whether each of the plurality of sensing units receives the corresponding reflected light.

In addition, the plurality of first incident lights is emitted toward a plurality of diagnosis points of the object to be diagnosed respectively; the plurality of second incident lights is emitted toward a plurality of reference points of the reference end respectively. The plurality of diagnosis points and the plurality of reference points reflect the plurality of first incident lights and the plurality of second incident lights respectively to form the plurality of reflected lights.

In fact, the plurality of optical units includes a fiber spectrum-dividing unit. When the coherent light enters into the light path structure, the coherent light is divided into two lights by the fiber spectrum-dividing unit, and then the plurality of optical units divides the two lights into the plurality of first incident lights and the plurality of second incident lights.

Another scope of the invention is to provide a large area optical diagnosis apparatus operating method. The second embodiment of the invention is a large area optical diagnosis apparatus operating method. In this embodiment, the large area optical diagnosis apparatus includes a light source, a light path structure, and a sensing module. The light path structure includes a plurality of optical units.

The method includes steps of: (a) the light source at least emitting a coherent light; (b) the light path structure dividing the coherent light into a plurality of first incident lights and a plurality of second incident lights, wherein the plurality of first incident lights is emitted toward an object to be diagnosed and the plurality of second incident lights is emitted toward a reference end; (c) the object to be diagnosed and the reference end reflecting the plurality of first incident lights and the plurality of second incident lights to be a plurality of reflected lights respectively; (d) the sensing module sensing the plurality of reflected lights to generate a sensing result related to the object to be diagnosed.

Compared to the prior arts, the large area optical diagnosis apparatus and operating method thereof in the invention can achieve the effect of simultaneous multi-point detection through the re-designed light path structure and sensing module without any rotation mirror designed in the light path to change the diagnosis points. Therefore, the large area optical diagnosis apparatus and operating method thereof in the invention can perform a large area diagnosis at the same time. Compared to the conventional time-domain or frequency-domain optical coherence tomography (OCT) diagnosis apparatuses, it can save a lot of time to largely enhance the diagnosis efficiency.

The advantage and spirit of the invention may be understood by the following detailed descriptions together with the appended drawings.

BRIEF DESCRIPTION OF THE APPENDED DRAWINGS

Figure 3:
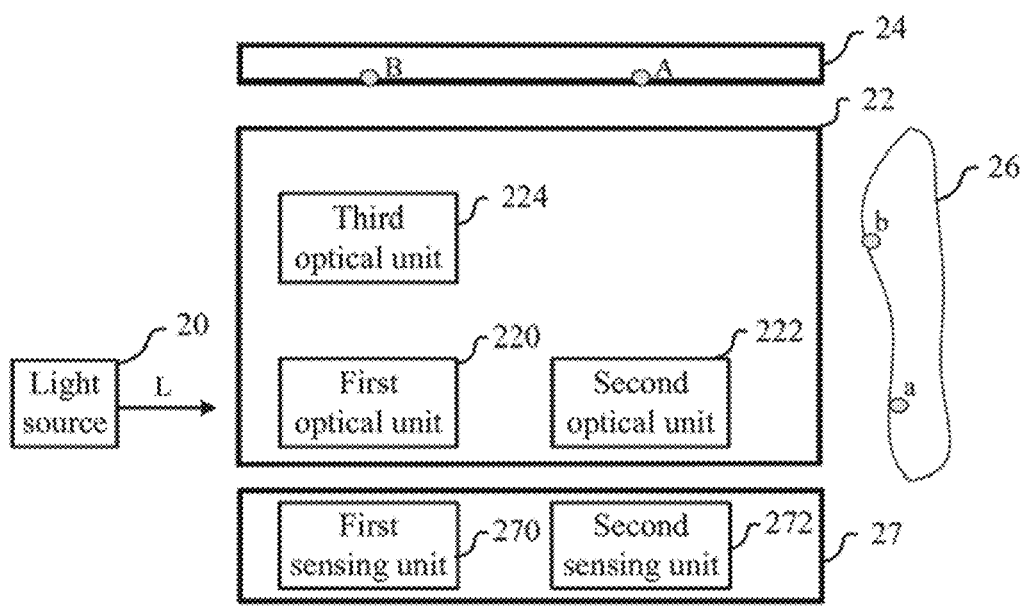
FIG. 3 illustrates a type of the light path structure of the large area optical diagnosis apparatus shown in FIG. 2.
Figure 4A:
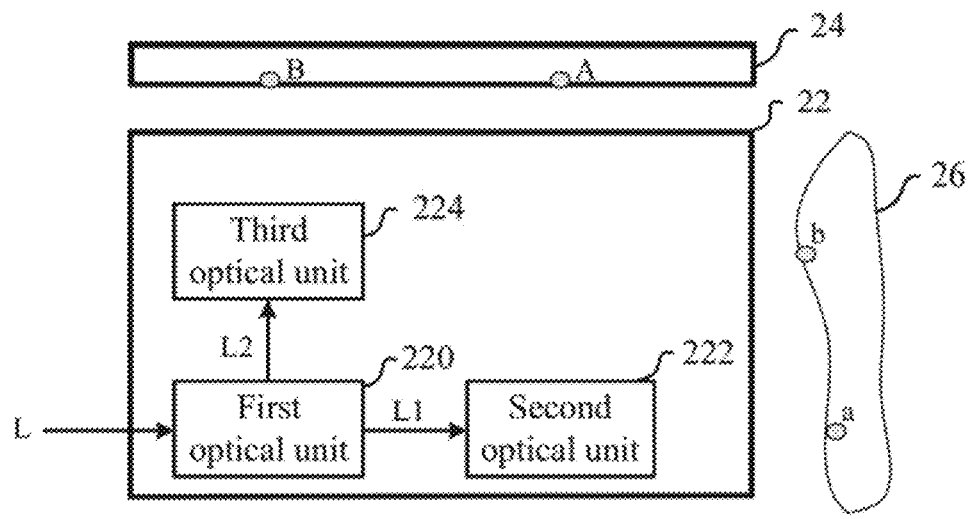
Figure 4B:
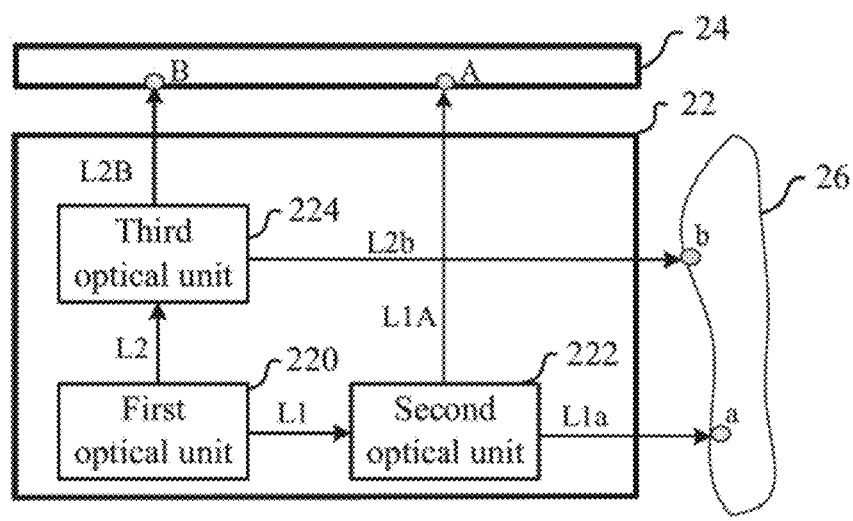
Figure 4C:
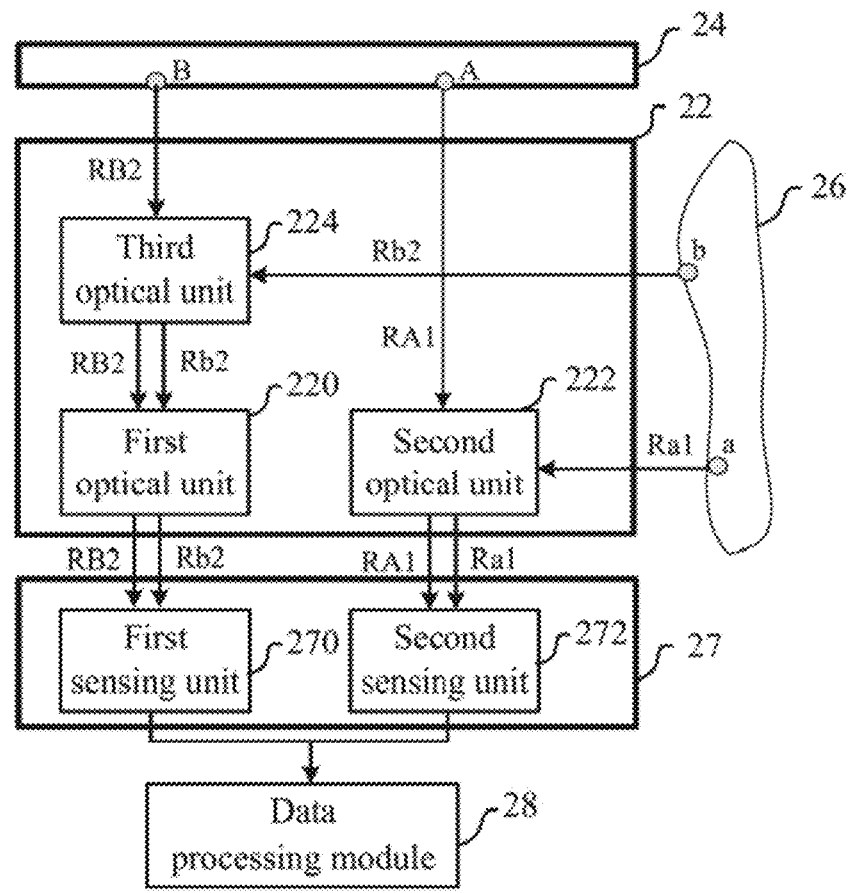

FIG. 4A~FIG. 4C illustrate the practical operation of the large area optical diagnosis apparatus shown in FIG. 3.

Figure 5:
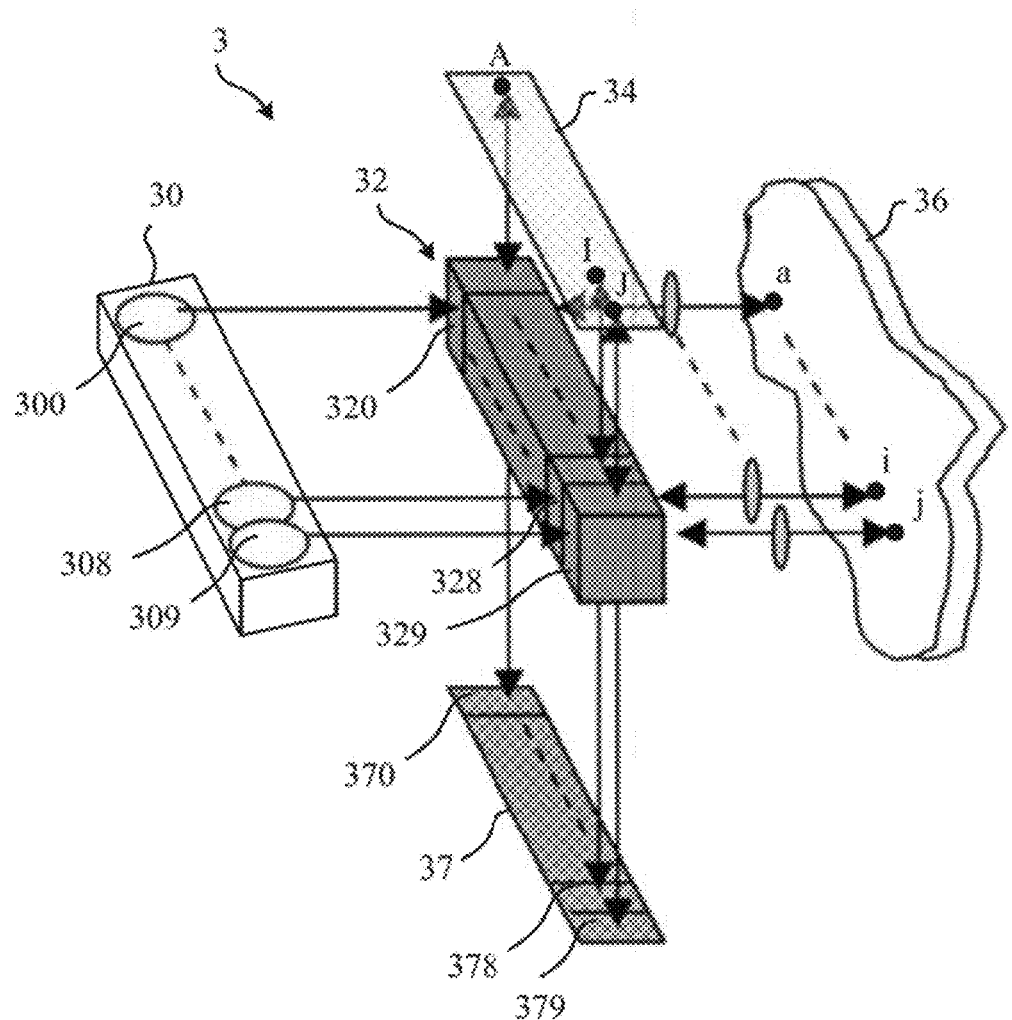

FIG. 5 illustrates a schematic figure of the large area optical diagnosis apparatus performing the large area optical cross-section diagnosis on the object to be diagnosed through a 1-D diagnosis way.

Figure 6A:
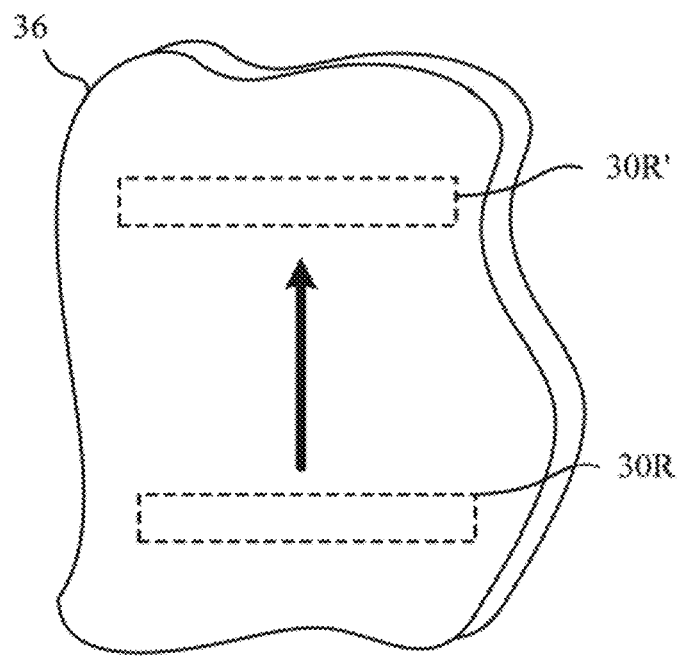

FIG. 6A illustrates a schematic figure of performing the large area optical cross-section diagnosis through a shifting way.

Figure 6B:
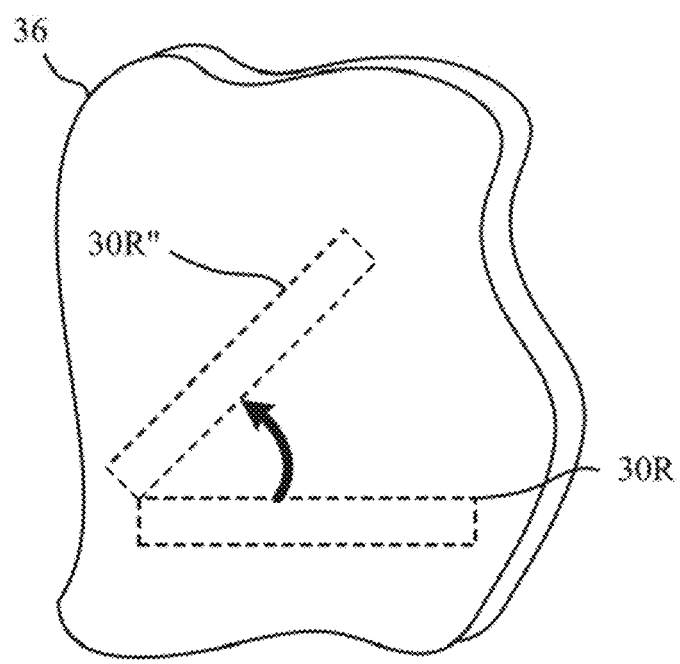

FIG. 6B illustrates a schematic figure of performing the large area optical cross-section diagnosis through a rotating way.

Figure 7:
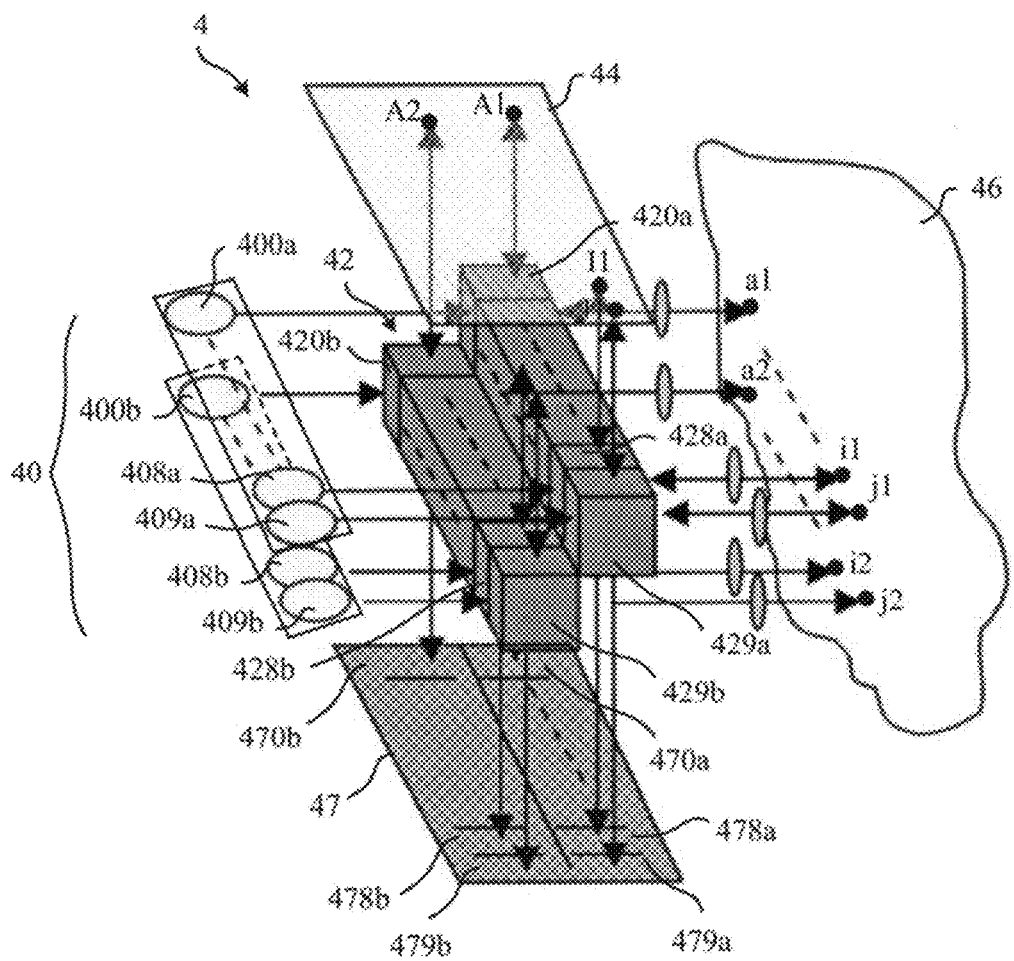

FIG. 7 illustrates a schematic figure of the large area optical diagnosis apparatus performing the large area optical cross-section diagnosis on the object to be diagnosed through a 2-D diagnosis way.

Figure 8:
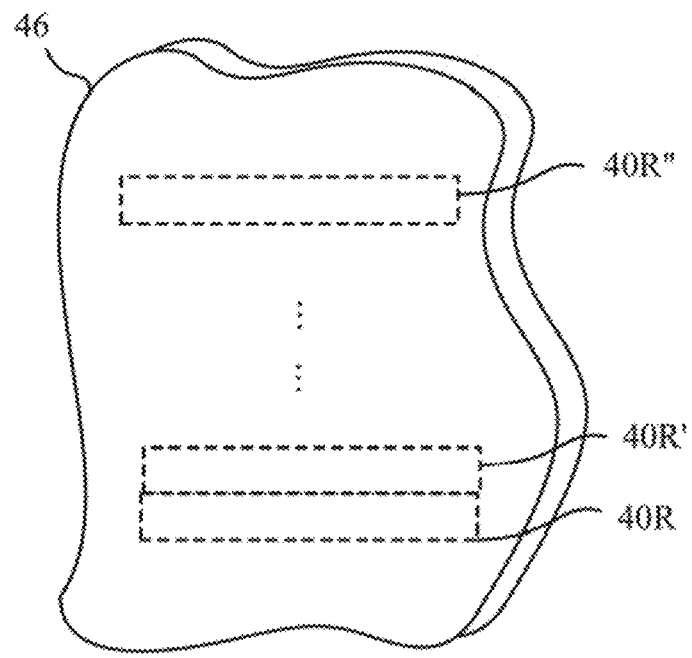

FIG. 8 illustrates a schematic figure of the large area optical diagnosis apparatus finishing the diagnosis on the 2-D area of the object to be diagnosed at the same time.

Figure 9:
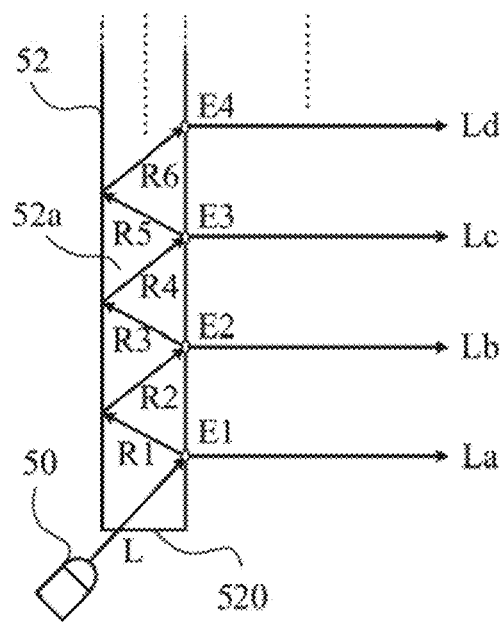

FIG. 9 illustrates another type of the light source of the large area optical diagnosis apparatus.

Figure 10:
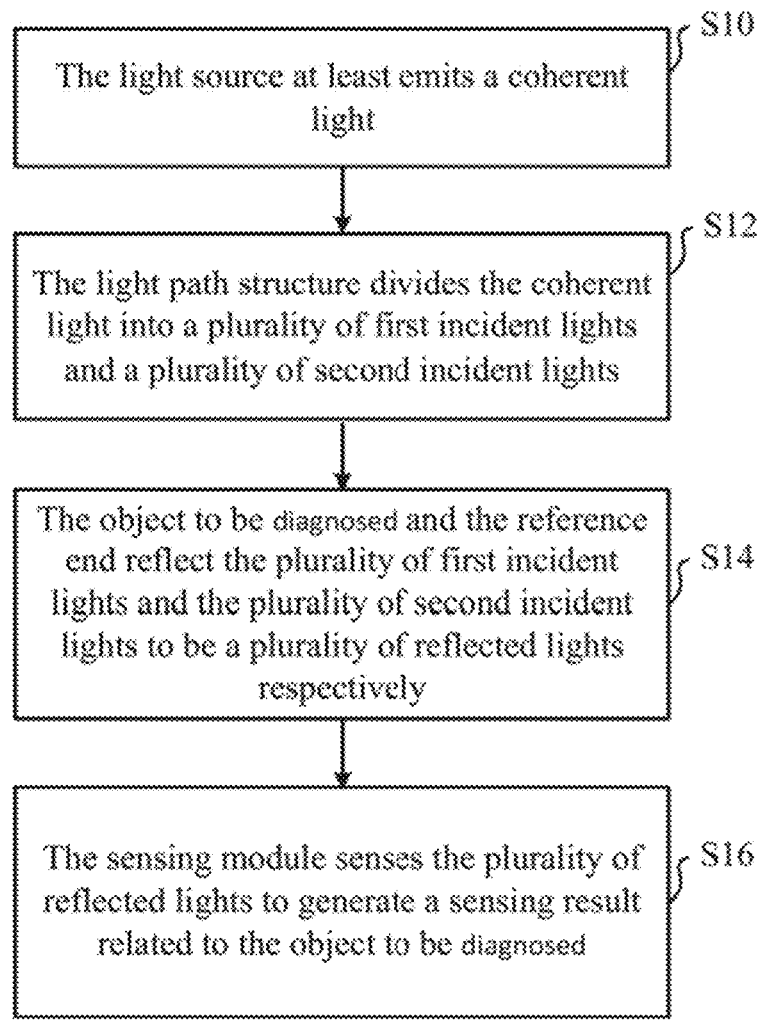

FIG. 10 illustrates a flowchart of the large area optical diagnosis apparatus operating method in the second embodiment of the invention.

DETAILED DESCRIPTION OF THE INVENTION

Figure 1:
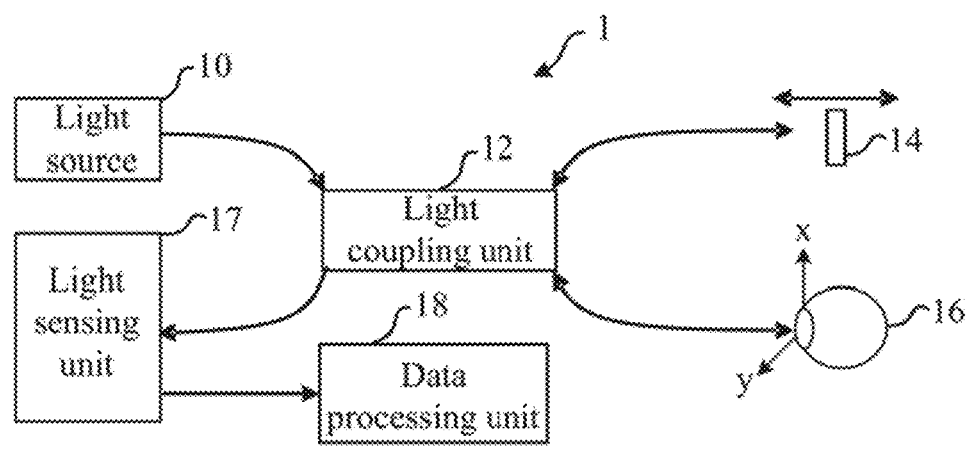
FIG. 1 illustrates a schematic figure of the basic structure of the conventional time-domain OCT diagnosis apparatus.
Figure 2:
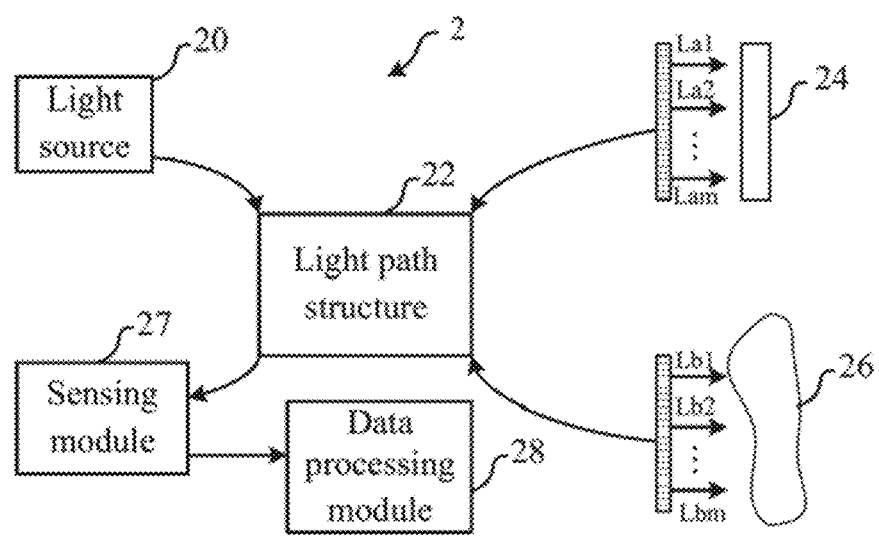
FIG. 2 illustrates a schematic figure of the large area optical diagnosis apparatus in the first embodiment of the invention.

The first embodiment of the invention is a large area optical diagnosis apparatus. In this embodiment, the large area optical diagnosis apparatus is used to diagnose an object to be diagnosed to obtain the optical data related to the vertical cross-section of the object to be diagnosed, but not limited to this. Please refer to FIG. 2. FIG. 2 illustrates a schematic figure of the large area optical diagnosis apparatus.

As shown in FIG. 2, the large area optical diagnosis apparatus 2 includes a light source 20, a light path structure 22, a reference end 24, an object to be diagnosed 26, a sensing module 27, and a data processing module 28. Wherein, the light source 20 at least emits a coherent light into the light path structure 22, and the light path structure 22 divides the coherent light into a plurality of first incident lights $La1$~$Lam$ and a plurality of second incident lights $Lb1$~$Lbm$. The plurality of first incident lights $La1$~$Lam$ is emitted to the reference end 24 and the plurality of second incident lights $Lb1$~$Lbm$ is emitted to the object to be diagnosed 26.

Then, the reference end 24 and the object to be diagnosed 26 reflect the plurality of first incident lights $La1$~$Lam$ and the plurality of second incident lights $Lb1$~$Lbm$ to be a plurality of reflected lights respectively emitted to the light path structure 22. Afterward, the sensing module 27 senses the plurality of reflected lights to generate a sensing result related to the object to be diagnosed 26. At last, the data processing module 28 generates an optical data related to a vertical cross-section of the object to be diagnosed 26 according to the sensing result.

It should be noticed that since the main feature of the invention is the different design types of the light path structure 22, then, the detail structure of the light path structure 22 will be further introduced. Please refer to FIG. 3. FIG. 3 illustrates a type of the light path structure 22 shown in FIG. 2.

As shown in FIG. 3, the light path structure 22 includes a first optical unit 220, a second optical unit 222, and a third optical unit 224, and their alignment condition can be seen in FIG. 3. The sensing module 27 includes a first sensing unit 270 and a second sensing unit 272. The reference end 24 includes reference points A and B. The object to be diagnosed 26 includes diagnosis points a and b. In practical applications, the first optical unit 220, the second optical unit 222, and the third optical unit 224 can be spectroscope or other apparatuses having the spectrum-dividing function. And, the light source 20 will emit a coherent light L to the light path structure 22.

Next, as shown in FIG. 4A, when the coherent light L is emitted into the first optical unit 220 of the light path structure 22, the first optical unit 220 will divide the coherent light L into a first divided light L1 and a second divided light L2, wherein the first divided light L1 is emitted to the second optical unit 222 and the second divided light L2 is emitted to the third optical unit 224.

Then, as shown in FIG. 4B, when the second optical unit 222 receives the first divided light L1, the second optical unit 222 will further divide the first divided light L1 into a first incident light L1$a$ and a second incident light L1A, wherein the first incident light L1$a$ is emitted to the diagnosis point a of the object to be diagnosed 26 and the second incident light L1A is emitted to the reference point A of the reference end 24.

Similarly, when the third optical unit 224 receives the second divided light L2, the third optical unit 224 will further divide the second divided light L2 into a first incident light L2b and a second incident light L2B, wherein the first incident light L2b is emitted to the diagnosis point b of the object to be diagnosed 26 and the second incident light L2B is emitted to the reference point B of the reference end 24.

Then, as shown in FIG. 4C, when the first incident light L1a is emitted to the diagnosis point a of the object to be diagnosed 26, the diagnosis point a of the object to be diagnosed 26 will reflect the first incident light L1a to form a first reflected light Ra1; when the second incident light L1A is emitted to the reference point A of the reference end 24, the reference point A of the reference end 24 will reflect the second incident light L1A to form a second reflected light RA1. Similarly, when the first incident light L2b is emitted to the diagnosis point b of the object to be diagnosed 26, the diagnosis point b of the object to be diagnosed 26 will reflect the first incident light L2b to form a first reflected light Rb2; when the second incident light L2B is emitted to the reference point B of the reference end 24, the reference point B of the reference end 24 will reflect the second incident light L2B to form a second reflected light RB2.

Wherein, the first reflected light Ra1 and the second reflected light RA1 are both emitted to the second optical unit 222; the first reflected light Rb2 and the second reflected light RB2 are both emitted to the third optical unit 224. Then, the second optical unit 222 will make the first reflected light Ra1 and the second reflected light RA1 emit to the second sensing unit 272 of the sensing module 27; the third optical unit 224 will make the first reflected light Rb2 and the second reflected light RB2 emit to the first sensing unit 270 of the sensing module 27 through the first optical unit 220.

Afterward, when the first sensing unit 270 of the sensing module 27 receives the first reflected light Rb2 and the second reflected light RB2, the first sensing unit 270 will generate a first sensing result accordingly. In fact, the first sensing result relates to the light path difference between the first reflected light Rb2 and the second reflected light RB2, but not limited to this case.

When the second sensing unit 272 of the sensing module 27 receives the first reflected light Ra1 and the second reflected light RA1, the second sensing unit 272 will generate a second sensing result accordingly. In fact, the second sensing result relates to the light path difference between the first reflected light Ra1 and the second reflected light RA1, but not limited to this case.

After the data processing module 28 receives the first sensing result and the second sensing result from the first sensing unit 270 and the second sensing unit 272 of the sensing module 27 respectively, the data processing module 28 will obtain the optical data related to the vertical cross-section of the object to be diagnosed 26 according to the above-mentioned first sensing result and the second sensing result.

It should be noticed that the first optical unit 220 of FIG. 3 can be also a fiber spectrum-dividing unit used to divide the coherent light L emitted from the light source 20 into two light paths, and then the galvo-mirrors, the reference points, and the sensing units corresponding to the two light paths respectively and the data processing module 28 are used to obtain the optical data related to the vertical cross-section of the object to be diagnosed 26.

In addition to the above-mentioned single light source embodiment, the light source of the invention can be also an array point light source used to emit a plurality of coherent lights including the coherent light, so that the large area optical diagnosis apparatus of the invention can perform a 2-D diagnosis on an area of the object to be diagnosed. Please refer to FIG. 5. FIG. 5 illustrates a schematic figure of the large area optical diagnosis apparatus 3 performing the large area optical cross-section diagnosis on the object to be diagnosed through the 1-D diagnosis way As shown in FIG. 5, the light source 30 includes point light sources 300~309 aligned in a 1-D array form; the light path structure 32 includes optical units 320~329; the sensing module 37 includes sensing units 370~379; the reference end 34 includes reference points A~J; the object to be diagnosed 36 includes the diagnosis points a~j. Wherein, the point light source 300, the optical unit 320, the sensing unit 370, the reference point A, and the diagnosis point a correspond to each other; the point light source 301, the optical unit 321, the sensing unit 371, the reference point B, and the diagnosis point b are corresponding to each other; and so on. By doing so, the large area optical diagnosis apparatus can finish the diagnosis on the 1-D area of the object to be diagnosed at the same time.

However, because the 1-D area on the object to be diagnosed 36 is only a small part of the entire 2-D area of the object to be diagnosed 36, the large area optical diagnosis apparatus still needs the shifting or rotating mechanism to diagnose the entire 2-D area of the object to be diagnosed 36. For example, in FIG. 6A, the shifting way is used to start the diagnosis from the 1-D area 30R of the object to be diagnosed 36 to the 1-D area 30R' to finish the diagnosis on the entire 2-D area of the object to be diagnosed 36. In FIG. 6B, the rotating way is used to start the diagnosis from the 1-D area 30R of the object to be diagnosed 36 to the 1-D area 30R" to finish the diagnosis on the entire 2-D area of the object to be diagnosed 36.

Please refer to FIG. 7. FIG. 7 illustrates a schematic figure of the large area optical diagnosis apparatus 4 performing the large area optical cross-section diagnosis on the object to be diagnosed 46 through a 2-D diagnosis way. As shown in FIG. 7, the light source 40 includes point light sources 400a~409a and 400b~409b aligned in a 2-D array form; the light path structure 42 includes optical units 420a~429a and 420b~429b; the sensing module 47 includes sensing units 470a~479a and 470b~479b; the reference end 44 includes reference points A1~J1 and A2~J2; the object to be diagnosed 46 includes the diagnosis points a1~j1 and a2~j2.

Wherein, the point light source 400a, the optical unit 420a, the sensing unit 470a, the reference point A1, and the diagnosis point a1 are corresponding to each other; the point light source 401a, the optical unit 421a, the sensing unit 471a, the reference point B1, and the diagnosis point b1 are corresponding to each other; the point light source 400b, the optical unit 420b, the sensing unit 470b, the reference point A2, and the diagnosis point a2 are corresponding to each other; the point light source 401b, the optical unit 421b, the sensing unit 471b, the reference point B2, and the diagnosis point b2 are corresponding to each other; and so on.

By doing so, the large area optical diagnosis apparatus can finish the diagnosis on the 2-D area of the object to be diagnosed 46 at the same time, as shown in FIG. 8, the diagnosis on the areas 40R~40R" on the object to be diagnosed 46 can be finished at the same time.

In addition, the light source of the large area optical diagnosis apparatus can also combine the optical units having light-guiding function to emit a plurality of parallel coherent lights. As shown in FIG. 9, after the incident lights L of the light source 50 is emitted into the light-guiding unit 52 from the left side outside the inlet 520, since the index of refraction of the light transmitting layer 52a in the light-guiding unit 52 is properly designed to be different from the index of refraction of the external medium, the incident lights L will generate several reflections (such as reflected lights R1~R6 )in the light transmitting layer 52a of the light-guiding unit 52 to emit a plurality of parallel first incident lights (coherent lights) La~Ld from outlets E1~E4.In practical applications, if the incident light emitted from the light source 50 can pass through the inlet 520 into the light-guiding unit 52, there is no other limitations for the position that the light source 50 disposed outside the light-guiding unit 52. Even the light-guiding unit 52 can have a plurality of light transmitting layers having different indexes of refraction to increase the distribution density of the parallel coherent lights emitted from the light guiding unit 52.

According to the above-mentioned embodiment, it can be known that the light source of the large area optical diagnosis apparatus in the invention can be any kinds of light source capable of at least emitting a coherent light into the light path structure without any other limitations.

The second embodiment of the invention is a large area optical diagnosis apparatus operating method. In practical applications, the large area optical diagnosis apparatus is used to diagnose the object to be diagnosed to obtain the optical data related to the vertical cross-section of the object to be diagnosed.

In this embodiment, the large area optical diagnosis apparatus includes a light source, a light path structure, and a sensing module. The light path structure includes a plurality of optical units. Please refer to FIG. 10. FIG. 10 illustrates a flowchart of the large area optical diagnosis apparatus operating method.

As shown in FIG. 10, the method includes following steps. Firstly, in step S10, the light source at least emits a coherent light. Then, in step S12, the light path structure divides the coherent light into a plurality of first incident lights and a plurality of second incident lights, wherein the plurality of first incident lights is emitted toward an object to be diagnosed and the plurality of second incident lights is emitted toward a reference end.

In step S14, the object to be diagnosed and the reference end reflect the plurality of first incident lights and the plurality of second incident lights to be a plurality of reflected lights respectively. Afterward, in step S16, the sensing module senses the plurality of reflected lights to generate a sensing result related to the object to be diagnosed.

In practical applications, the sensing module can include a plurality of sensing units corresponding to the plurality of reflected lights respectively. The sensing module generates the sensing result according to whether each of the plurality of sensing units receives the corresponding reflected light.

In addition, the plurality of first incident lights is emitted toward a plurality of diagnosis points of the object to be diagnosed respectively, the plurality of second incident lights is emitted toward a plurality of reference points of the reference end respectively, the plurality of diagnosis points and the plurality of reference points reflect the plurality of first incident lights and the plurality of second incident lights respectively to form the plurality of reflected lights.

In fact, the plurality of optical units can include a fiber spectrum-dividing unit, when the coherent light enters into the light path structure, the coherent light is divided into two lights by the fiber spectrum-dividing unit, and then the plurality of optical units divides the two lights into the plurality of first incident lights and the plurality of second incident lights. It should be noticed that the light source of the large area optical diagnosis apparatus in the invention can be any kinds of light source capable of at least emitting a coherent light into the light path structure without any other limitations. For example, the light source can be an array point light source used for emitting a plurality of coherent lights including the coherent light, so that the large area optical diagnosis apparatus can perform a 2-D diagnosis on a area of the object to be diagnosed, and the area can be reached via a shifting or rotating mechanism, but not limited to this case.

Compared to the prior arts, the large area optical diagnosis apparatus and operating method thereof in the invention can achieve the effect of simultaneous multi-point detection through the re-designed light path structure and sensing module without any rotation mirror designed in the light path to change the diagnosis points. Therefore, the large area optical diagnosis apparatus and operating method thereof in the invention can perform a large area diagnosis at the same time. Compared to the conventional time-domain or frequency-domain optical coherence tomography (OCT) diagnosis apparatuses, it can save a lot of time to largely enhance the diagnosis efficiency.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A large area optical diagnosis apparatus, comprising:
a light source for emitting at least one incident light;
a light-guiding unit comprising a plurality of light transmitting layers having different indexes of refraction, an inlet, and a plurality of outlets, the inlet being disposed on a first surface of the light-guiding unit, the plurality of outlets being disposed on a second surface of the light-guiding unit, the first surface being adjacent and connected to the second surface, the indexes of refraction of the plurality of light transmitting layers being different from the index of refraction of the external medium, when the at least one incident light is emitted into the light-guiding unit from the inlet on the second surface, the at least one incident light will be reflected several times in the plurality of light transmitting layers and then emitted out of the light-guiding unit from the plurality of outlets to form a plurality of parallel coherent lights;
a light path structure comprising a plurality of optical units used for dividing the plurality of coherent lights into a plurality of first incident lights and a plurality of second incident lights, the plurality of first incident lights being emitted toward an object to be diagnosed and the plurality of second incident lights being emitted toward a reference end, the object to be diagnosed and the reference end reflecting the plurality of first incident lights and the plurality of second incident lights to be a plurality of reflected lights respectively; and
a sensing module comprising a plurality of sensing units, for sensing the plurality of reflected lights to generate a sensing result related to the object to be diagnosed;
wherein the light source comprises a plurality of point light sources, the reference end comprises a plurality of reference points, the object to be diagnosed comprises a plurality of diagnosis points; one of the plurality of point light sources, one of the plurality of optical units, one of the plurality of sensing units, one of the plurality of reference points, and one of the plurality of diagnosis points correspond to each other, the large area optical diagnosis apparatus performs a diagnosis on the plurality of diagnosis points via a rotating mechanism.

2. The large area optical diagnosis apparatus of claim 1, wherein the a plurality of sensing units correspond to the plurality of reflected lights respectively, the sensing module generates the sensing result according to whether each of the plurality of sensing units receives the corresponding reflected light.

3. The large area optical diagnosis apparatus of claim 1, wherein the plurality of first incident lights is emitted toward the plurality of diagnosis points of the object to be diagnosed respectively, the plurality of second incident lights is emitted toward the plurality of reference points of the reference end respectively, the plurality of diagnosis points and the plurality of reference points reflect the plurality of first incident lights and the plurality of second incident lights respectively to form the plurality of reflected lights.

4. The large area optical diagnosis apparatus of claim 1, wherein the plurality of optical units comprises a fiber spectrum-dividing unit, when the plurality of coherent lights enter into the light path structure, each of the plurality of the coherent lights is divided into two lights by the fiber spectrum-dividing unit, and then the plurality of optical units divides the two lights into the plurality of first incident lights and the plurality of second incident lights.

5. The large area optical diagnosis apparatus of claim 1, wherein the light source is an array point light source.

6. A method of operating a large area optical diagnosis apparatus, the large area optical diagnosis apparatus comprising a light source, a light-guiding unit, a light path structure, and a sensing module, the light path structure comprising a plurality of optical units, the light-guiding unit comprising a plurality of light transmitting layers having different indexes of refraction, an inlet, and a plurality of outlets, the inlet being disposed on a first surface of the light-guiding unit, the plurality of outlets being disposed on a second surface of the light-guiding unit, the first surface being adjacent and connected to the second surface, the indexes of refraction of the plurality of light transmitting layers being different from the index of refraction of the external medium, the sensing module comprising a plurality of sensing units, the method comprising steps of:

(a) the light source emitting at least one incident light;

(a1) when the at least one incident light is emitted into the light-guiding unit from the inlet on the second surface, the at least one incident light will be reflected several times in the plurality of light transmitting layers and then emitted out of the light-guiding unit from the plurality of outlets to form a plurality of parallel coherent lights;

(b) the light path structure dividing the plurality of coherent lights into a plurality of first incident lights and a plurality of second incident lights, wherein the plurality of first incident lights is emitted toward an object to be diagnosed and the plurality of second incident lights is emitted toward a reference end;

(c) the object to be diagnosed and the reference end reflecting the plurality of first incident lights and the plurality of second incident lights to be a plurality of reflected lights respectively; and (d) the sensing module sensing the plurality of reflected lights to generate a sensing result related to the object to be diagnosed via the plurality of sensing units;

wherein the light source comprises a plurality of point light sources, the reference end comprises a plurality of reference points, the object to be diagnosed comprises a plurality of diagnosis points; one of the plurality of point light sources, one of the plurality of optical units, one of the plurality of sensing units, one of the plurality of reference points, and one of the plurality of diagnosis points correspond to each other, the method performs a diagnosis on the plurality of diagnosis points via a rotating mechanism.

7. The method of claim 6, wherein the plurality of sensing units correspond to the plurality of reflected lights respectively, the sensing module generates the sensing result according to whether each of the plurality of sensing units receives the corresponding reflected light.

8. The method of claim 6, wherein the plurality of first incident lights is emitted toward the plurality of diagnosis points of the object to be diagnosed respectively, the plurality of second incident lights is emitted toward the plurality of reference points of the reference end respectively, the plurality of diagnosis points and the plurality of reference points reflect the plurality of first incident lights and the plurality of second incident lights respectively to form the plurality of reflected lights.

9. The method of claim 6, wherein the plurality of optical units comprises a fiber spectrum-dividing unit, when the plurality of coherent lights enter into the light path structure, each of the plurality of the coherent lights is divided into two lights by the fiber spectrum-dividing unit, and then the plurality of optical units divides the two lights into the plurality of first incident lights and the plurality of second incident lights.

10. The method of claim 6, wherein the light source is an array point light source.

* * * * *